United States Patent [19]
Fuchs

[11] Patent Number: 6,032,926
[45] Date of Patent: Mar. 7, 2000

[54] HOSE COUPLING FOR A MEDICAL TRANSFER SYSTEM

[75] Inventor: Juergen Fuchs, Bad Emstal, Germany

[73] Assignee: B. Braun Melsungen AG, Melsungen, Germany

[21] Appl. No.: 09/222,825

[22] Filed: Dec. 30, 1998

[30] Foreign Application Priority Data

Jan. 7, 1998 [DE] Germany ................ 298 00 107 U

[51] Int. Cl.[7] ................ F16L 29/00; A61M 5/00
[52] U.S. Cl. .................. 251/149.4; 251/149.1; 604/167; 604/256
[58] Field of Search ............. 251/149.1, 149.8, 251/149.4; 285/320; 604/256, 167, 283

[56] References Cited

U.S. PATENT DOCUMENTS

| | | | |
|---|---|---|---|
| 5,344,414 | 9/1994 | Lopez et al. | 604/283 |
| 5,674,206 | 10/1997 | Allton et al. | 251/149.1 X |
| 5,775,671 | 7/1998 | Cote, Sr. | 251/149.1 |

Primary Examiner—Kevin Lee
Attorney, Agent, or Firm—Diller, Ramik & Wight, PC

[57] ABSTRACT

A hose coupling comprises a coupling element with a throughflow channel and a plug member with a plug projection for insertion into the throughflow channel of the coupling element. The plug projection opens a valve when inserted. To retain the plug member on the coupling element, detents are used that each have a locking nose engaging behind a retaining member. Thereby, withdrawing the plug member is inhibited. The plug member may take a second position in which the plug projection does not yet push open the valve, but already seals the throughflow channel. Thus, additional hose clamps may be omitted.

11 Claims, 2 Drawing Sheets

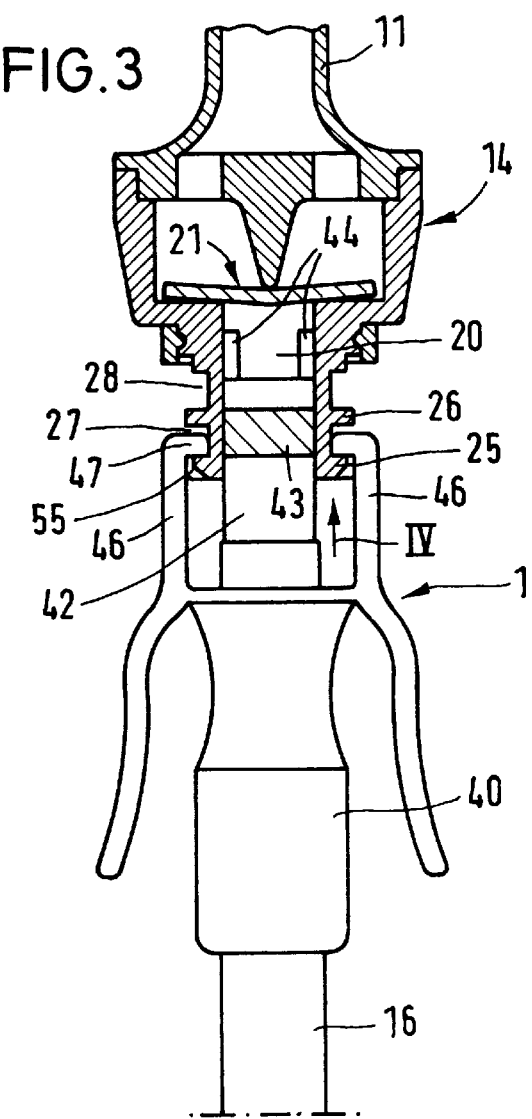
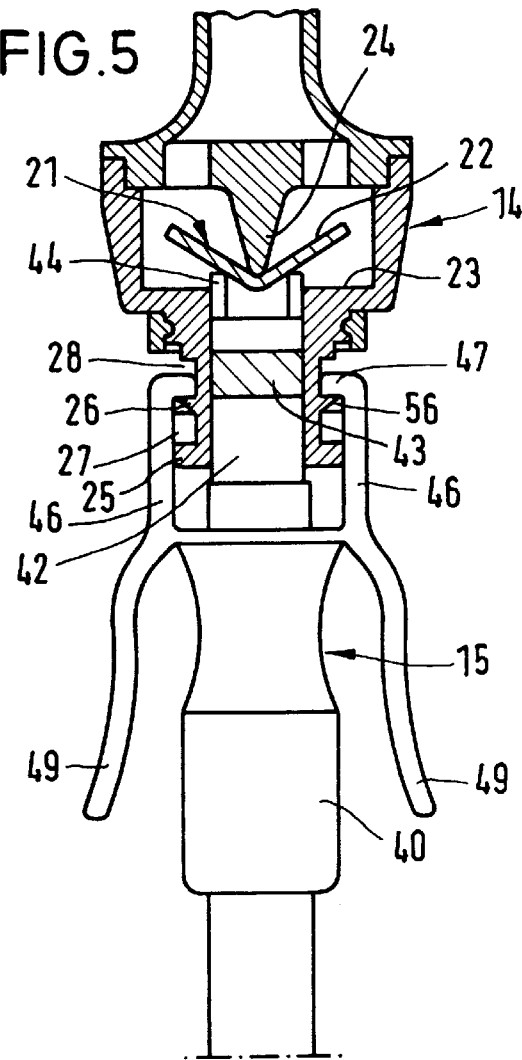
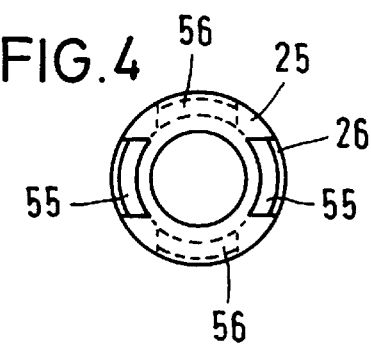

HOSE COUPLING FOR A MEDICAL TRANSFER SYSTEM

BACKGROUND ART

The present invention refers to a hose coupling for a medical transfer system, for example for taking medicinal solutions from a bag or a bottle.

For taking liquids from a bag or another receptacle, it is common practice to provide the receptacle with an outlet nozzle containing a diaphragm in the shape of a rubber plug. This diaphragm is pierced with the piercing thorn of a transfer device. Through a channel provided in the piercing thorn, the liquid flows into the piercing thorn and a hose connected thereto. However, piercing thorns entail several disadvantages. Piercing the diaphragm with the piercing thorn, for example, requires considerable force. Further, injuries may be caused by the tip of the piercing thorn. Moreover, the piercing thorn may disengage particles from the diaphragm that may get into the liquid. It is an advantage that the diaphragm, after withdrawing the piercing thorn, heals again to form a tight seal.

Further, hose couplings for medical transfer systems are known, which are provided with Luer lock closures and allow for disconnection. However, such hose couplings do not allow for rotary movement at the transfer system since this would risk an inadvertent disconnection.

SUMMARY OF THE INVENTION

It is an object of the present invention to provide a hose coupling for a medical transfer system that requires no piercing thorn, seals itself again after disconnection, and cannot be opened by rotary movement at the transfer system.

The hose coupling of the present invention comprises coupling element with a throughflow channel, a plug member being connectable with the coupling element. The coupling element comprises a valve pushed into the open state by a plug projection of the plug member. A retaining member is provided on the coupling element for allowing a locking device of the plug member to catch when the plug projection keeps the valve open. Thus, the plug member locks with the coupling element in the open position of the valve so that it cannot be removed without special measures. Due to the locking, the plug member is held to the coupling element even if the transfer system is rotated, for example, by twisting the corresponding hoses. The coupling engagement cannot be broken by such rotary movements. Disengaging the coupling ultimately requires a manual operation of a releasing device. It is essential that the plug member snappingly engages with the coupling element, i.e. that the coupling is not merely effected by clamping, but by a locking element snapping over a retaining member. Thus, the hose coupling is secured against inadvertent disconnection.

The hose coupling of the present invention may be made at low cost from injection molded plastic parts. Plastics materials on the basis of polyolefines should be used.

Preferably, the first retaining member is an annular collar comprising at least one insertion bevel surmountable by the locking device and resisting the withdrawal thereof. Because of the annular collar, the plug member may be turned at will relative to the coupling element, without the coupling being broken or becoming leaky.

According to a preferred embodiment of the invention, the coupling element is provided with a second retaining member making it possible for the locking device on the plug member to lock on when the plug projection is accommodated in the throughflow channel in a sealing manner, but does not yet push the valve open. Thus, it becomes possible to preparatorily connect the plug member with the coupling element without any flow of liquid therethrough. Therefore, there is no need for providing a sliding clamp or another blocking element in the hose of the transfer system to prevent liquid from flowing immediately after the connection between the transfer system and the transfer receptacle is made. The plug member has two locking positions on the coupling element, the passage between the throughflow channel and the plug member being sealed hermetically to the outside in both locking positions. However, both positions differ in that the valve is open in the one position, whereas it is closed in the other.

Basically, it is possible to design the lock as a ball locking device, wherein a certain force limit has to be overcome to disengage the locked connection or to move from one locking position to the other. Preferably, the locking device is designed such that it comprises a detent means engaging a saw-tooth structure, the saw-tooth structure being overcome automatically in the push-on direction of the detent, whereas, in the direction of withdrawal, the saw-tooth structure prevents the detent from being pulled off. By actuating a releasing lever, the locking device may be cleared for withdrawal. This offers the advantage of additional security against inadvertent disconnection by pulling the components apart. This security is even increased if the locking device has two detents with a respective releasing lever for each. In this case, both releasing levers have to be actuated simultaneously to break the locking.

To prevent an erroneous setting of the wrong locking position upon coupling the plug member to the coupling element, the retaining members may each have an insertion bevel surmountable by the locking device, the insertion bevel of the one retaining member being circumferentially shifted with respect to the insertion bevel of the other retaining member. As a consequence, the axial insertion movement allows only for a locking in the ready position. To set the operational position, i.e. the open position of the valve, the plug member has to be rotated and pushed on further.

BRIEF DESCRIPTION OF THE DRAWINGS

The following is a detailed description of a preferred embodiment of the present invention in conjunction with the accompanying drawings.

In the Figures:

FIG. 3 illustrates the hose coupling in the coupled state and in the ready position, FIG. 4 is a front view of the end of the coupling element, seen in the direction of the arrow IV in FIG. 3, and FIG. 5 shows the hose coupling in the operational position, with the valve open.

DETAILED DESCRIPTION OF A PREFERRED EMBODIMENT

Figure 1:
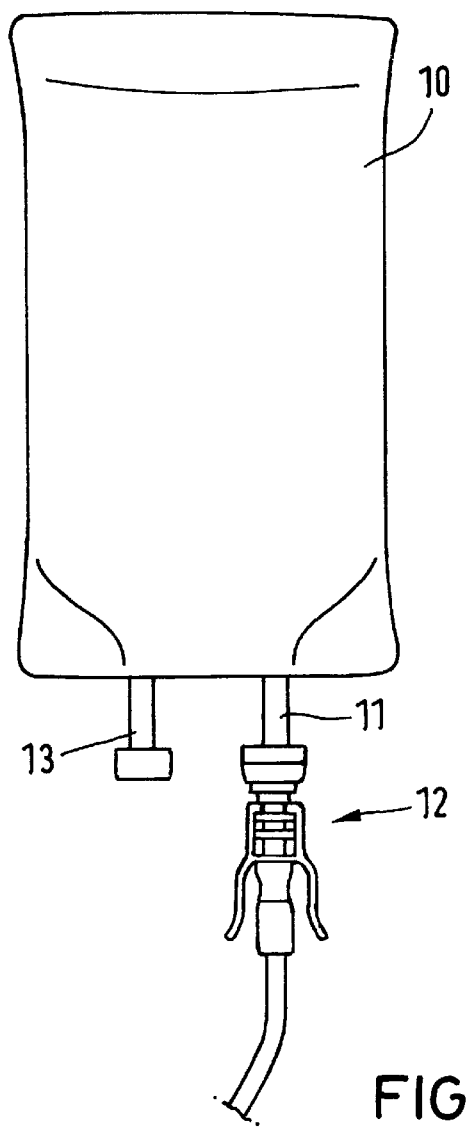
FIG. 1 illustrates a bag containing a washing solution with a transfer system coupled thereto.

FIG. 1 illustrates a bag 10 containing a washing solution to be transfused into the body of a patient. To this end, the bag is suspended from a suspension device, with the outlet nozzle 11 being directed downward. The hose coupling 12 is provided at the outlet nozzle 11. Further, the bag 10 has a rubber plug to allow other media to be injected thereinto.

Figure 2:
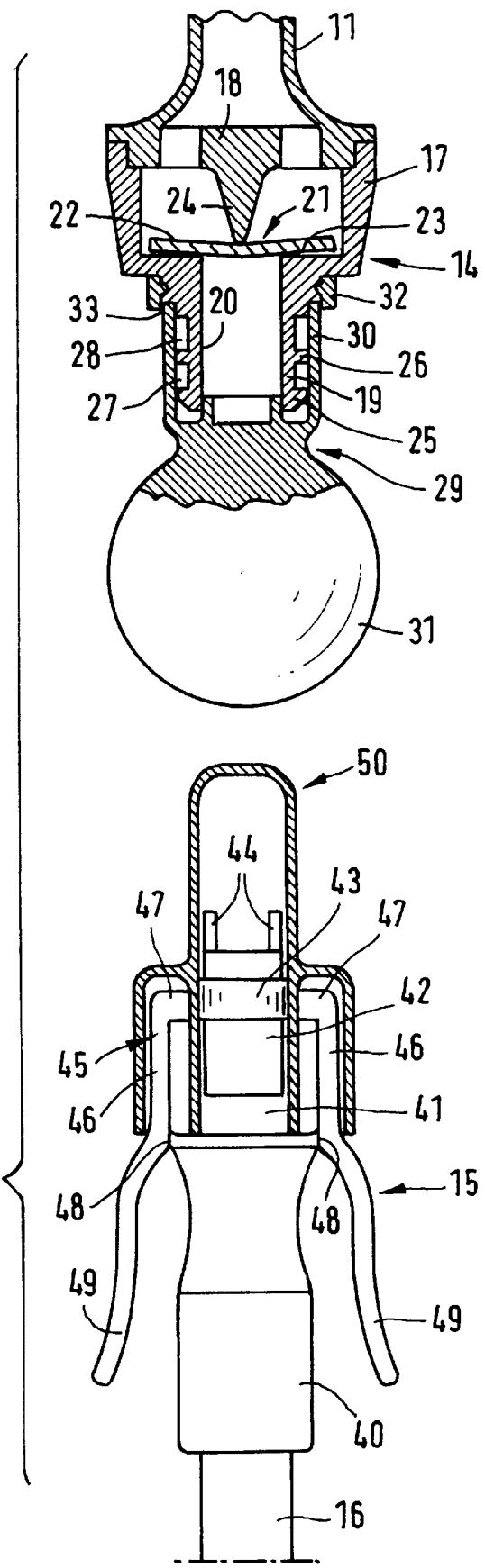
FIG. 2 shows the two parts of the hose coupling when separated and each having a protective cap.

As illustrated in FIG. 2, the hose coupling 12 comprises a coupling element 14 connected with the outlet nozzle 11 of the bag, and a plug member 15 connected with a transfer hose 16 and adapted to be coupled to the coupling element 14.

The coupling element 14 comprises a housing 17 delimited towards the outlet nozzle 11 by a perforated wall 18, while a tubular coupling projection 19 extends towards the opposite end. A cylindrical throughflow channel 20 extends through the coupling projection 19. One end of the through flow channel 20 is provided with a valve 21 in the form of an elastic disc 22, the edge of which presses against a valve seat 23 surrounding the end of the throughflow channel 20. The tip of a thorn 24 presses on the center portion of the disc 22 so that the disc 22 is bent slightly and forcibly pressed against the seat 23 in a sealing manner.

The coupling projection 19 has two retaining members 25, 26, each being formed as a continuous annular collar. An annular groove 27 is formed between the retaining members 25 and 26, and another annular groove 28 is located between the retaining member 26 and the housing 17.

In the shipping state, a closure cap 29 sits on the coupling projection 19, the cap having a cylindrical cap portion 30 and a hand knob 31. The cap portion 30 is connected with a ring 32 fastened to the housing 17. A rated breaking point 33 is provided between the cap portion 30 and the ring 32, forming a germ-tight closure. In this way, the cap 29 provides a germ-tight enclosure for the coupling projection 19. When it is desired to open the closure, the closure cap 29 is twisted, whereby it is torn off at the rated breaking point 33. The plug member 15 comprises a housing body 40 connected with the hose 16 in a sealing manner and having a protective cap seat 41 at the opposite end. A cylindrical plug projection 42 extends axially from the protective cap seat 41. A sealing ring 43 is set or molded onto the plug projection 42. Ridges 44 extend axially from the end of the plug projection 42. The ridges 44 are situated opposite each other, shifted by 180°.

Further, the plug member 15 comprises a locking device 45 of two detents 46 that are opposite each other by 180° and have inwardly directed locking noses 47. The detents are each connected to the housing 40 via a plastics hinge 48 and they pass into a releasing lever 49 projecting rearward on the sides of the housing 40. The plastics hinges 48 bias the detents 46 such that the locking noses 47 are pressed against the plug projection 42. By manually pressing the releasing levers 49 against the housing 40, the detents 46 are pivoted into the open position.

The plug projection 42 is surrounded by a protective cap 50 clamped to the protective cap seat 41 and enclosing the plug projection in a germ-tight manner. Before the coupling is made, the protective cap 50 is pulled off.

FIG. 3 shows the first coupling state the plug member 15 assumes when it is first preparatorily coupled to the coupling element 14, however, without opening the valve 21. The plug projection 42 is fitted into the throughflow channel 20, with the seal 43 sealing the throughflow channel to the outside. During insertion, the locking noses 47 meet the insertion bevels 55 of the retaining member 25. Thereby, the detents 45 are spread apart until the locking noses 47 lock in the annular groove 27. Advancing them further is inhibited by the retaining member 26, even when both releasing levers 49 are actuated. In this state, the ridges 44 are still spaced from the valve 21. No liquid flows from the coupling element 14 to the plug member 15. A channel (not illustrated) extends through the tubular plug projection 42 and the housing, which channel is in communication with the lumen of the hose 16.

FIG. 4 shows the two insertion bevels 55 that are disposed on the annular retaining member 25 and are situated opposite each other, shifted by 180°. Thus, the plug member 15 has to be set to the coupling element in a very specific rotational position so that the locking noses 47 can slide on the insertion bevels 55.

The annular retaining member 26 is also provided with two insertion bevels 56 which are shifted by 90° with respect to the insertion bevels 55 (FIG. 4).

When turning the plug member 15 by 90°, it may be advanced further from the position illustrated in FIG. 3 so that its plug projection 42 enters deeper into the throughflow passage 20 and the ridges 44 push the valve 21 open. Thereby, the disc 22 is deformed in V-shape above the thorn 24, whereby it is lifted from the seat 24 and clears the passage from the housing 17 into the throughflow channel 20. When pushing the plug projection 42 further, the locking noses 47 slide over the insertion bevels 56 so as to finally lock behind the retaining member 26. Thereby, the plug member 15 is locked to the coupling element 14. In this position, the plug member 15 may be rotated about its axis at will without the locking becoming disengaged. Such rotation is also possible in the position illustrated in FIG. 3.

To disengage the coupling, the two releasing levers 49 are pressed against each other. Thereby, the locking noses 47 are disengaged from the retaining members 26 an 25, respectively, so that the plug member 15 may be pulled from the coupling element 14.

Although the present invention has been described in conjunction with a preferred embodiment thereof, it is obvious to an expert in the field that various changes and modifications can be made thereto. These changes and modifications are considered to fall into the scope of the present invention as defined by the appended claims.

What is claimed is:

1. A hose coupling for a medical transfer system comprising a coupling element (14) having a throughflow channel (20), a plug member (15) including a plug portion (42) adapted to be inserted into the throughflow channel (20) in sealed relationship thereto, a valve (21) being arranged in the coupling element (14) for normally closing the throughflow channel (20), the valve (21) being adapted to be pushed open by inserting the plug projection (42) into the flow channel (20), a first rest member (26) provided on an exterior of the coupling element (14) for allowing pair of a locking devices (45) of the plug member (15) to lock thereon when the plug projection (42) is inserted a predetermined distance into the throughflow channel (20) to directly contact and push the valve (21) open, said pair of locking devices (45) each including a releasing lever (49) and opposite thereto a plurality of locking noses (47) for engaging said first rest member (26) to effect locking between the coupling element (14) and the plug member (15), said coupling element (14) and said plug member (15) being freely rotatable relative to each other in the open position of said valve (21), and the axial distance between the locking noses (47) and an end (44) of said plug projection (42) being greater than the axial distance between said valve (21) and said first rest member (26) whereby the locking noses (47) engage the first rest member (26) as the valve (21) is pushed open by the plug projection end (44).

2. The hose coupling as defined in claim 1 wherein the first rest member (26) is an annular collar having at least one insertion bevel (56).

3. The hose coupling as defined in claim 1 wherein the coupling element (14) is provided with a second rest member (25) in axially spaced relationship to said first rest member (26) with which said locking noses (47) engage without the valve (21) being pushed open.

4. The hose coupling as defined in claim 1 wherein the coupling element (14) is provided with a second rest member (25) in axially spaced relationship to said first rest member (26) with which said locking noses (47) engage without the valve (21) being pushed open, and said second rest member (25) is a second annular collar having at least one insertion bevel (56).

5. The hose coupling as defined in claim 1 wherein the coupling element (14) is provided with a second rest member (25) in axially spaced relationship to said first rest member (26) with which said locking noses (47) engage without the valve (21) being pushed open, and said second rest member (25) is a second annular collar having at least one insertion bevel (56) disposed in circumferentially offset relationship to said insertion bevel (56) of said first rest member (26).

6. The hose coupling as defined in claim 1 wherein said plug projection end (44) is a radially projecting ridge.

7. The hose coupling as defined in claim 1 wherein said valve (21) is an elastic disk having a central portion and a circumferential portion outboard thereof, and said coupling element (14) includes an annular seat (23) upon which seats said valve circumferential portion and a projection (24) directed towards said valve center portion.

8. The hose coupling as defined in claim 2 wherein said valve (21) is an elastic disk having a central portion and a circumferential portion outboard thereof, and said coupling element (14) includes an annular seat (23) upon which seats said valve circumferential portion and a projection (24) directed towards said valve center portion.

9. The hose coupling as defined in claim 3 wherein said valve (21) is an elastic disk having a central portion and a circumferential portion outboard thereof, and said coupling element (14) includes an annular seat (23) upon which seats said valve circumferential portion and a projection (24) directed towards said valve center portion.

10. The hose coupling as defined in claim 4 wherein said valve (21) is an elastic disk having a central portion and a circumferential portion outboard thereof, and said coupling element (14) includes an annular seat (23) upon which seats said valve circumferential portion and a projection (24) directed towards said valve center portion.

11. The hose coupling as defined in claim 5 wherein said valve (21) is an elastic disk having a central portion and a circumferential portion outboard thereof, and said coupling element (14) includes an annular seat (23) upon which seats said valve circumferential portion and a projection (24) directed towards said valve center portion.

* * * * *